(12) United States Patent
Hong et al.

(10) Patent No.: US 8,187,829 B2
(45) Date of Patent: May 29, 2012

(54) METHOD FOR FABRICATING PATTERN ON A BIOSENSOR SUBSTRATE AND BIOSENSOR USING THE SAME

(75) Inventors: Hyobong Hong, Daejeon (KR); Hyungjoong Yoon, Gyeonggi-do (KR); Myungae Chung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 368 days.

(21) Appl. No.: 12/466,451

(22) Filed: May 15, 2009

(65) Prior Publication Data

US 2009/0283426 A1 Nov. 19, 2009

(30) Foreign Application Priority Data

May 16, 2008 (KR) .................. 10-2008-0045547

(51) Int. Cl.
G01N 33/00 (2006.01)
(52) U.S. Cl. ........................................ 435/7.92
(58) Field of Classification Search .................. None
See application file for complete search history.

(56) References Cited

U.S. PATENT DOCUMENTS

| | | | |
|---|---|---|---|
| 4,194,912 A * | 3/1980 | Davidson | 430/322 |
| 5,252,743 A | 10/1993 | Barrett et al. | |
| 5,510,270 A | 4/1996 | Fodor et al. | |
| 2003/0162185 A1 * | 8/2003 | Melnyk et al. | 435/6 |
| 2004/0067530 A1 * | 4/2004 | Gruner | 435/7.1 |
| 2007/0134713 A1 * | 6/2007 | Cao | 435/6 |

FOREIGN PATENT DOCUMENTS

| | | |
|---|---|---|
| JP | 2006-53092 | 2/2006 |
| KR | 10-2003-0023192 A | 3/2003 |
| KR | 10-2004-0040789 | 5/2004 |
| KR | 10-2005-0098588 | 10/2005 |
| KR | 10-2006-0084736 A | 7/2006 |
| KR | 10-2007-0113557 A | 11/2007 |

OTHER PUBLICATIONS

Steven W. Metzger, et al., "Development and Characterization of Surface Chemistries for Microfabricated Biosensors," J. Vac. Sci. Technol. A 17(5), Sep. 1999, pp. 2623-2628.
Dongmei Xu, et al, "Preparation of Polyethyleneimine Nanogels via Photo-Fenton Reaction," Shanghai Institute of Applied Physics, Feb. 2007, pp. 1606-1611.

* cited by examiner

Primary Examiner — N C Yang
Assistant Examiner — Richard Moerschell
(74) Attorney, Agent, or Firm — Staas & Halsey LLP

(57) ABSTRACT

The present invention relates to a method for fabricating a pattern on a biosensor substrate and a biosensor using the same. The present invention provides a method of fabricating a pattern on a substrate of a biosensor in which an amine group is formed on a substrate by using polyethylenimine (PEI), and a site to which a biosubstance is immobilized is masked and irradiated with ultraviolet rays, such that a pattern having a desired shape can be formed on the substrate and a biosensor in which the biosubstance is immobilized on the pattern acquired by using the above-mentioned method.

4 Claims, 5 Drawing Sheets

METHOD FOR FABRICATING PATTERN ON A BIOSENSOR SUBSTRATE AND BIOSENSOR USING THE SAME

RELATED APPLICATIONS

The present application claims priority to Korean Patent Application Serial Number 10-2008-0045547, filed on May 16, 2008, the entirety of which is hereby incorporated by reference.

BACKGROUND OF THE INVENTION

1. Field of the Invention

The present invention relates to a method for fabricating a pattern on a biosensor substrate and a biosensor using the same.

2. Description of the Related Art

A biosensor is an element that can selectively detect a substance to be analyzed by transducing biological interaction and recognition reaction into an electric or optical signal through a combination of a biological receptor having a recognition function of a specific substance with an electrical or optical transducer. Herein, the substance includes general chemicals in addition to biosubstances such as DNA and blood sugar. The biological receptor, as a biosubstance that serves to generate a signal measurable by the transducer while selectively recognizing the analyzed substance, includes enzyme, protein, DNA, cell, hormone, a biomembrane, a tissue, etc. Various physicochemical methods such as electrochemical, optical, magnetic, piezoelectric, electronic methods, etc. are adopted to transduce the generated biosignal or recognition reaction into useful signals, such that an electrical signal is ultimately obtained. The biosensor reversibly recognizes a specific substance to thereby enable successive measurement. The biosensor may include a biosensor that irreversibly recognizes the specific interaction like an antigen-antibody interaction or hybrid formation of DNA. Such biosensor that has a concept as a detector is classified into a biochip. However, recently, defining between the biosensor and the biochip has been ambiguous and technical compatibility therebetween is being actively progressed, such that the biosensor and the biochip are not particularly differentiated from each other.

Immobilizing bioactive compounds onto a specific spot of the biosensor is required to fabricate the biosensor. Most of the biosensors are constituted by a substrate, a chemical linker, and a biological interface. Glass, quartz, silicon wafer, or polymer is generally used as the substrate. However, these substrates do not have a specific binding characteristic for binding directly with the biosubstance. Therefore, modification of a surface is required in order to bind the substrate with the biological interface.

The chemical linker having the specific binding characteristic may be generated on or added to the surface of the substrate at the time of modifying the substrate itself or adding various reagents to an organic film. For surface modification, the related art is based on physical absorption, chemical binding, ligand-receptor binding, and a combination thereof. Selection of the art for achieving the above-mentioned object is based on a specific chemical or physical characteristic of the substrate and/or biological interface. Even though a lot of chemicals and materials are used for modifying the substrate, most of the materials and chemicals that function as the chemical linker must have bi-functionality to bind both the substrate and the biological interface.

Polyethylenimine (PEI) is one of the polymers used for achieving the above-mentioned object. The polymer may be used for immobilizing cells, DNAs, and proteins in addition to transfection of cell lines. PEI is the branched polymer having a high-density amine group. Pure PEI, which contains plural amines, may be covalently bound with other molecules such as succinimidyl ester, sulfonyl chloride, and isothiocyanate mainly used as a linker between the film and a bioactive compounds. Further, PEI is known to be immobilized onto a silicon oxide film through spontaneous absorption. These characteristics make PEI into a material suitable for modifying the surface.

In the related art, a technique using an etching process was used as a method of immobilizing the biosubstance by patterning. For example, in a method of immobilizing polypeptide onto the substrate by using a photolithography process, a mask having each pattern must be fabricated whenever fabricating a chip, and cleaning and mask arraying processes must be performed for each process. As a result, the process becomes complicated and expensive equipment is required, such that cost becomes high. Moreover, the related art was limitative in a pattern design and not environmentally-friendly.

In immobilizing the biosubstance onto the substrate, an immobilization rate of the biosubstance must be high and the biosubstance must be immobilized in a desired pattern (preferably, a minute pattern). In particular, it is more important to integrate and immobilize the biosubstance onto a specific spot of a micrometer scale with high density as possible. In the case in which the biosubstance is integrated with high density, the ability of deciphering genetic information is improved as much. However, in order to spot or apply the biosubstance to a very small spot of the sensor, a very expensive equipment such as a micro-arrayer is required. The reason for this is that a sensing element of the biosensor occupies the very small spot. Even though the entire sensor is large, the size of the spot is generally in the range of nm to μm. Therefore, development of a new method for immobilization or attachment is required.

As a result, the present inventors have completed the present invention by finding that the amine group on the PEI layer formed on the surface of the substrate is eliminated to lose a binding capability with succinimidyl ester by UN irradiation and that the surface of the substrate is patterned, and verifying a signal of a substance (i.e., streptavidin) selectively bounded with a biosubstance (i.e., biotin) that is immobilized onto the patterned surface.

SUMMARY OF THE INVENTION

Accordingly, an object of the present invention is to provide a method for fabricating a pattern on a biosensor substrate.

Another object of the present invention is to provide a biosensor in which a biosubstance is immobilized onto the pattern on the biosensor substrate fabricated by the above-mentioned method.

A further object of the present invention is to provide a method for detecting a target substance bound with a biosubstance using the biosensor.

In order to achieve the above-mentioned object, the present invention provides a method for fabricating a pattern on a biosensor substrate that includes:

(a) depositing a silicon oxide film on a substrate;
(b) forming a polyethylenimine layer on the silicon oxide film;

(c) selectively masking a site where a biosubstance is immobilized onto the polyethylenimine layer; and (d) irradiating the substrate by using ultraviolet rays.

In the present invention, the substrate is comprised of any one selected from the group consisting of silicon, quartz, and glass.

In the present invention, the masking is performed by using any one selected from the group consisting of a teflon tape, an aluminum foil, and an enamelled copper wire.

In the present invention, the irradiation is performed for 10 minutes to 1 hour by using ultraviolet rays of 220 nm to 300 nm.

The present invention also provides a biosensor in which a biosubstance is immobilized onto the pattern on the substrate fabricated by the above-mentioned method.

In the present invention, the biosubstance is immobilized onto the substrate through a linker that forms a covalent bond with an amine-reactive group.

In the present invention, the amine-reactive group is one or more group selected from the group consisting of carboxylic acid ester, acid chloride, sulfonyl chloride, anhydride, ketone, aldehyde, halo, isothiocyanate, thioisocyanate, epoxide, activated hydroxyl group, olefin, carboxyl, succinimidyl ester, sulfosuccinimidyl ester, maleimido, epoxy, and ethenesulfonyl group.

In the present invention, the biosubstance is one selected from a group consisting of enzyme, protein, DNA, RNA, microorganism, animal and plant cells and organs, and nerve cells.

The present invention provides a method for detecting a target substance bound with a biosubstance using a biosensor, comprising; (i) applying a specimen containing the target substance to the biosensor; and (ii) detecting the target substance specifically bound with the biosubstance on the biosensor.

Hereinafter, the present invention will be described in detail.

A method for fabricating a pattern on a biosensor substrate according to the present invention will be stepwise described below.

A method for fabricating a patterned biosensor substrate includes:

(a) depositing a silicon oxide film on a substrate;

(b) forming a polyethylenimine layer on the silicon oxide film;

(c) selectively masking a predetermined site where a biosubstance is immobilized onto the polyethylenimine layer; and (d) irradiating the substrate by using ultraviolet rays.

The substrate used in the present invention on which an adhesive film may be formed is not particularly limited, but in particular, it is preferable that the substrate is comprised of anyone selected from the group consisting of glass, quartz, silicon wafer, etc. in order to form a PEI layer. It is preferable that the substrate is used after being cleansed and dried by conventional methods such as an RCA method, etc.

In the present invention, the silicon oxide ($SiO_2$) film is deposited on the substrate. The reason for this, PEI may be immobilized onto the silicon oxide film through spontaneous absorption. The deposition of the silicon oxide film may be performed by, for example, thermal CVD method, etc. The thickness of the layer is preferably in the range of approximately 500 Å to 2000 Å, but is not limited thereto.

As described above, the substrate having the silicon oxide film formed thereon is dipped in a polyethylenimine (PEI) solution for 1 to 6 hours and preferably for 2 to 4 hours, thereby forming an amine group on the substrate.

As described above, a mask with a shape of a pattern to be formed is disposed on the substrate with the amine group formed thereon. At this time, the mask is a mask for performing masking with respect to the UV. A light-impermeable material is not limited as a material of the mask. The shape of the mask is not limited depending on a shape to be patterned. For instance, the mask may have a plate shape or a line shape. In the present invention, a tape made of teflon is used and in addition, aluminum foil, enamelled copper wire, etc. may be used, but the material of the mask is not limited thereto. Further, in the present invention, the shape of the pattern is not limitative. For example, the pattern may have various shapes such as linear, circular, triangular, quadrangular shapes, etc. depending on the purpose and integration of the biosubstance to be immobilized. In addition, the patterns such as circle, triangle, quadrangle, etc. may be arranged such as a checkered board shape. Further, in the case of the surface pattern of the present invention, a diameter (in the case of circle) or the length of one side (in the case of triangle and quadrangle) may have at least 5 micrometers (μm). As a specific example, they may have 20 micrometers (μm) to 100 micrometers (μm) at the time of fabricating DNA or cell chips.

When the substrate in which the mask is disposed is irradiated by using light including an ultraviolet (hereinafter, also referred to as 'UV') range, the amine group on the unmasked surface is removed. It is assumed that this is caused by a structural change. For the UV irradiation, irradiation is performed for 10 minutes to 1 hours by using a light source that can irradiate ultraviolet rays within an ultraviolet ray range, preferably ultraviolet rays having a wavelength range of 220 nm to 300 nm, and more preferably ultraviolet rays having a short wavelength of 260 nm or less, such that the light source can be a product easily accessible on the market. Further, the surface and the light source are preferably close to each other so as to maximize the intensity of energy reaching the surface. For example, the distance between the surface and the light source is equal to or shorter than 2 cm and more preferably may be 0.5 cm. As described above, the substrate irradiated with ultraviolet rays may be instantly used without postprocessing. That is, it is not necessary to perform steps such as etching, peeling, etc. performed after forming the pattern in the known photolithography.

Since the amine group is attached onto the pattern fabricated as above, that is, the masked part as it is, the biosubstance is immobilized by using the amine group to be used as the biosensor. Therefore, the present invention provides a biosensor in which a biosubstance is immobilized onto the pattern on the substrate fabricated by the above-mentioned method.

In the present invention, the biosubstance is immobilized onto the substrate by a linker that forms a covalent bond with an amine-reactive group. In the present invention, a linker having a succinimidyl ester group at one end and biotin at the other end is immobilized and bound with magnetic particles coated with streptabidin, such that the substrate may be bound with the biosubstance. However, the present invention is not limited thereto. The linker is immobilized onto the surface by reacting with a functional group on the surface of the chip and at the same time, the linker totally represents a compound having a reactive group at the end thereof, which can have coupling reaction with the functional group of the biosubstance. The amine-reactive group is one or more group selected from the group consisting of carboxylic acid ester, acid chloride, sulfonyl chloride, anhydride, ketone, aldehyde, halo, isothiocyanate, thioisocyanate, epoxide, activated hydroxyl group, olefin, carboxyl, succinimidyl ester, sulfosuccinimidyl ester, maleimido, epoxy, and ethenesulfonyl group.

The present invention also provides a method for detecting a target substance bound with a biosubstance using a biosensor, which includes (i) applying a specimen by flowing the specimen containing the target substance to the biosensor fabricated as above or dipping the biosensor in the specimen solution; and (ii) detecting the target substance specifically bound with the biosubstance on the biosensor.

In the present invention, the biosubstance immobilized onto the substrate generally has a specific characteristic to specifically react with the target substance to be generally analyzed. For example, in the case when the biosubstance is nucleic acid, the biosubstance can interact with target nucleic acid having complementary nucleotide sequences through hybridization reaction. In the case when the biosubstance is protein, the biosubstance and the target substance can specifically interact with each other through antigen-antibody reaction, ligand-receptor interaction, enzyme-substrate interaction, etc. Further, in the case when the biosubstance is polysaccharide, the biosubstance may be specifically recognized by protein or antibody that recognizes polysaccharide. By using a detection system that can detect the specific interaction between the biosubstance and the target substance and the interaction result, the biosensor that can be acquired by immobilizing the biosubstance onto the substrate may be used for various analyses.

In a method for fabricating a pattern of the present invention, a PEI layer is formed and irradiated with ultraviolet rays, such that a pattern having a desired shape may be formed on a substrate of a biosensor. Therefore, it is possible to overcome disadvantages in the known technology of fabricating a pattern on a biosensor substrate, which requires a complicated process and expensive equipment. Moreover, since the biosubstance is immobilized after the pattern on a substrate is fabricated, it is advantageous in that an immobilization rate of the biosubstance can increase.

DESCRIPTION OF THE PREFERRED EMBODIMENTS

Hereinafter, embodiments of the present invention will be described in detail with reference to the accompanying drawings. However, the embodiments are used to exemplify the present invention. The present invention may be variously modified and changed without being limited by the embodiments.

Embodiment 1

Formation of a Pattern on a Substrate of Biosensor

Figure 1:
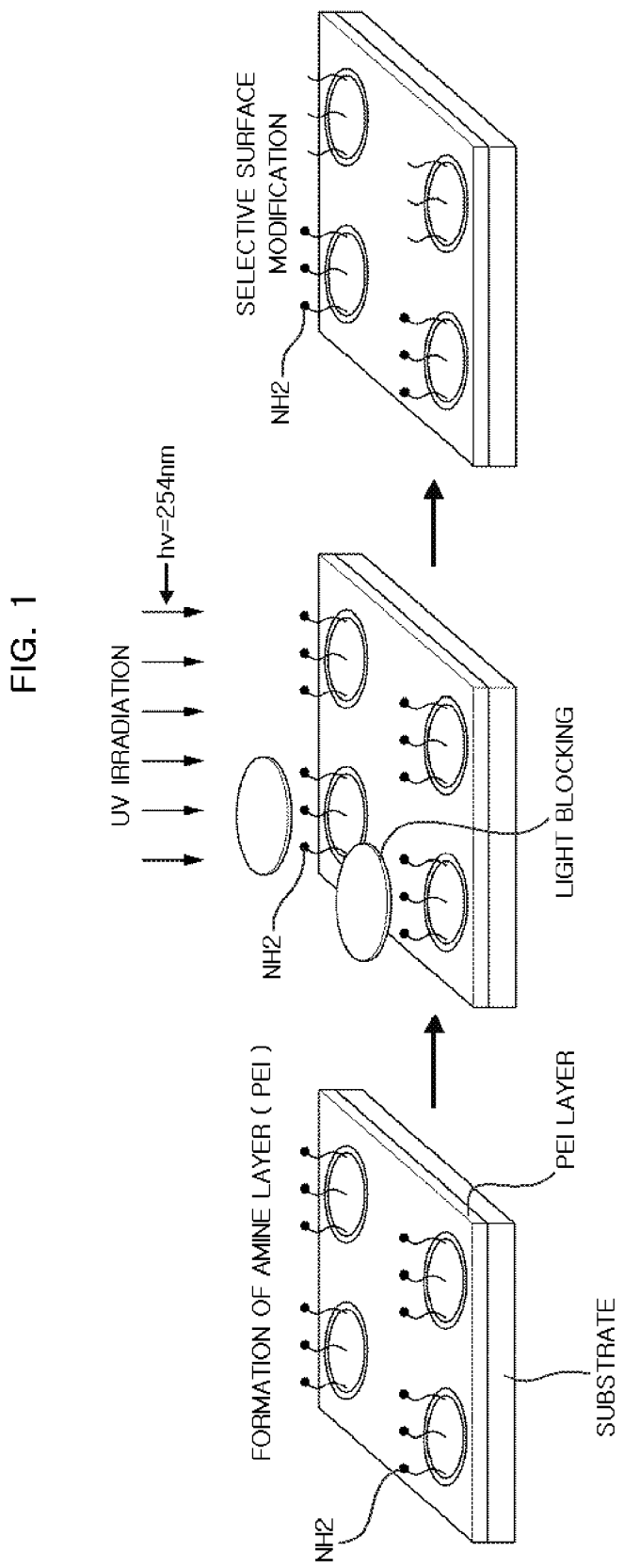
FIG. 1 is a schematic diagram illustrating a method for fabricating a pattern on a biosensor substrate according to a preferred embodiment of the present invention.

FIG. 1 illustrates a schematic diagram of the embodiment. An $SiO_2$ film (10.0 nm) was thermally deposited on a silicon wafer (Nano Fab Center, Daejeon, Korea). A specimen was fabricated by cutting the sample by a size of 1 cm×1 cm. The organic substance of the specimen was eliminated by a general RCA method (first, cleaning is performed with a solution ($NH_4OH:H_2O_2$: deionized water=1:1:5) in a heating bath having a temperature of 380K in order to eliminate an organic substance on an $SiO_2$ surface for 10 minutes. Thereafter, cleaning is performed with a solution ($HCl:H_2O_2$:deionized water=1:1:5) in the heating bath having the temperature of 380K for 10 minutes in order to eliminate a heavy metal element existing on the surface.). The surface of the specimen was transformed in a silanol form by using MeOH:HCl (1:1 v/v) solution. The surface of an Si-wafer was coated with a PEI layer by a dipping method in which the surface is dipped in a 10% PEI (cat #. P3143, SIGMA, USA) solution dissolved in 50 mM $Na_2CO_3$ (pH 8.2) for 3 hours. After incubation, an excessive quantity of PEI was eliminated with deionized water and moisture was eliminated with nitrogen gas. A teflon tape having a specific pattern, a cross shape crossing on the substrate in the embodiment, was attached onto the surface of the substrate to which the biosubstance will be immobilized. In a dark room, the silicon wafer was irradiated with ultraviolet rays of 254 nm for 1 hour. A distance between the silicon wafer and a UV lamp (Spectroline, ENF-260 C, USA) was 0.5 cm.

Experimental Example 1

Analysis of Surface Characteristics

Two methods described below are used in order to measure formation of a pattern on a substrate by UV.

[Analysis Using Fluorescent Microscopy]

In order to verify an effect of UV irradiation onto the surface, analysis is performed using the fluorescent microscopy. For this experiment, AMCA-X,SE [6-((7-amino-4-methylcoumarin-3-acetyl)amino)hexanoic acid, succinimidyl ester] (Anaspec, USA) was used, which consists of succinimidyl ester at one end of a molecule and a fluorescent compound having a maximum absorption wavelength at 354 nm and a maximum emission wavelength at 442 nm at the other end of the molecule. AMCA-X,SE has succinimidyl ester at the end of moiety as one of fluorescent molecules which are most widely used for tagging a biosubstance. Therefore, AMCA-X,SE may react with molecules containing amine such as antibody and protein in an aqueous solution. An aminohexanoyl space may also reduce quenching of fluorophore during conjugation.

An AMCA-X,SE stock was prepared by dissolving 10 mg AMCA-X,SE in 1.0 ml DMSO. Before application onto the surface, the stock solution was mixed with amine-free phosphate buffer saline (PBS) at a ratio of 25:75. The substrate prepared in Embodiment 1 was dipped into the solution and incubated for 30 minutes. Lastly, the sample was dried with argon gas. A fluorescent image was obtained by using a microscope equipped with a fluorescent source having an emission wavelength of 350 nm. If fluorescence is not observed at a site exposed by UV or fluorescence is observed at a blocked site on the same substrate, an effect of UV irradiation to the amine group of the substrate is proved.

Figure 2:
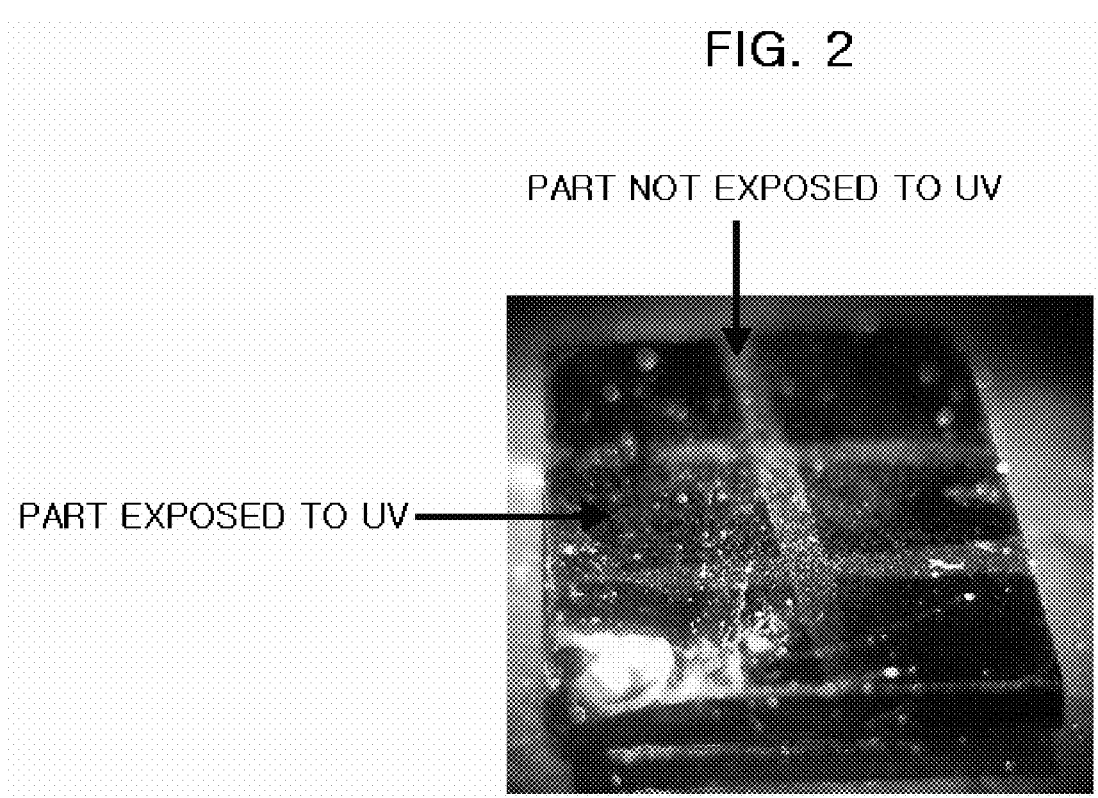
FIG. 2 is a photograph in which a pattern on a biosensor substrate is observed by using a fluorescent microscopy according to a preferred embodiment of the present invention. A part unexposed to UV is formed in a cross pattern.
Figure 3:
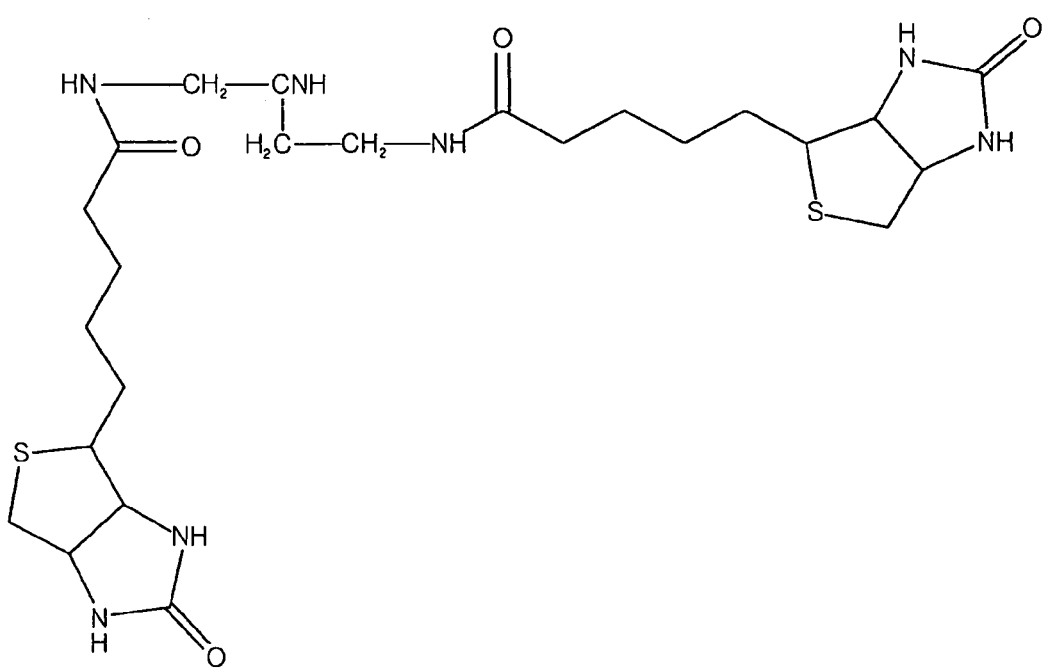
FIG. 3 is a molecular structure in which polyethylenimine and NHS-biotin are bound with each other.

According to the observation result using the fluorescent microscopy, an UV irradiation part did not show any fluorescence, but fluorescence was observed at a UV blocking portion which is covered with a teflon tape (see FIG. 2). On the basis of the result, amine and AMCA-X,SE are selectively bound at the UV blocking portion, that is, a pattern forming portion.

[AR-XPS Analysis]

For verification of a chemical binding state on a PEI-coated surface and quantification, AR-XPS (Axis-NOVA, Kratos, UK) and sulfosuccinimidyl-6-[biotin-amino]hexane (NHS-Sulfo-biotin, PIERCE, USA) are used. The reason for this is that the molecule is one of molecules that are widely used as a chemical linker for the biosubstance and the molecule contains not the compositional element of the silicon wafer and the PEI but sulfur.

Before measurement, a specimen was dipped in a solution in which 2.2 mg NHS-Sulfo-Biotin was dissolved in a 500 µl PBS buffer (pH. 7.4) for 30 minutes. Thereafter, the specimen was rinsed with deionized water and dried with nitrogen gas. Monochromatic Al-Ka (1486.6 eV) was used as a radiation source for the XPS analysis. In addition, a hemispherical analyzer was used. Anode power was maintained at 75 W (5 mA, 15 kV) in the range of UHV ($1.0 \times 10^{-9}$ Torr). In order to increase surface sensitivity, AR-XPS was performed while changing take-off angles (TOAs) across the range of 0 to 60° with respect to the analyzer.

Figure 4:
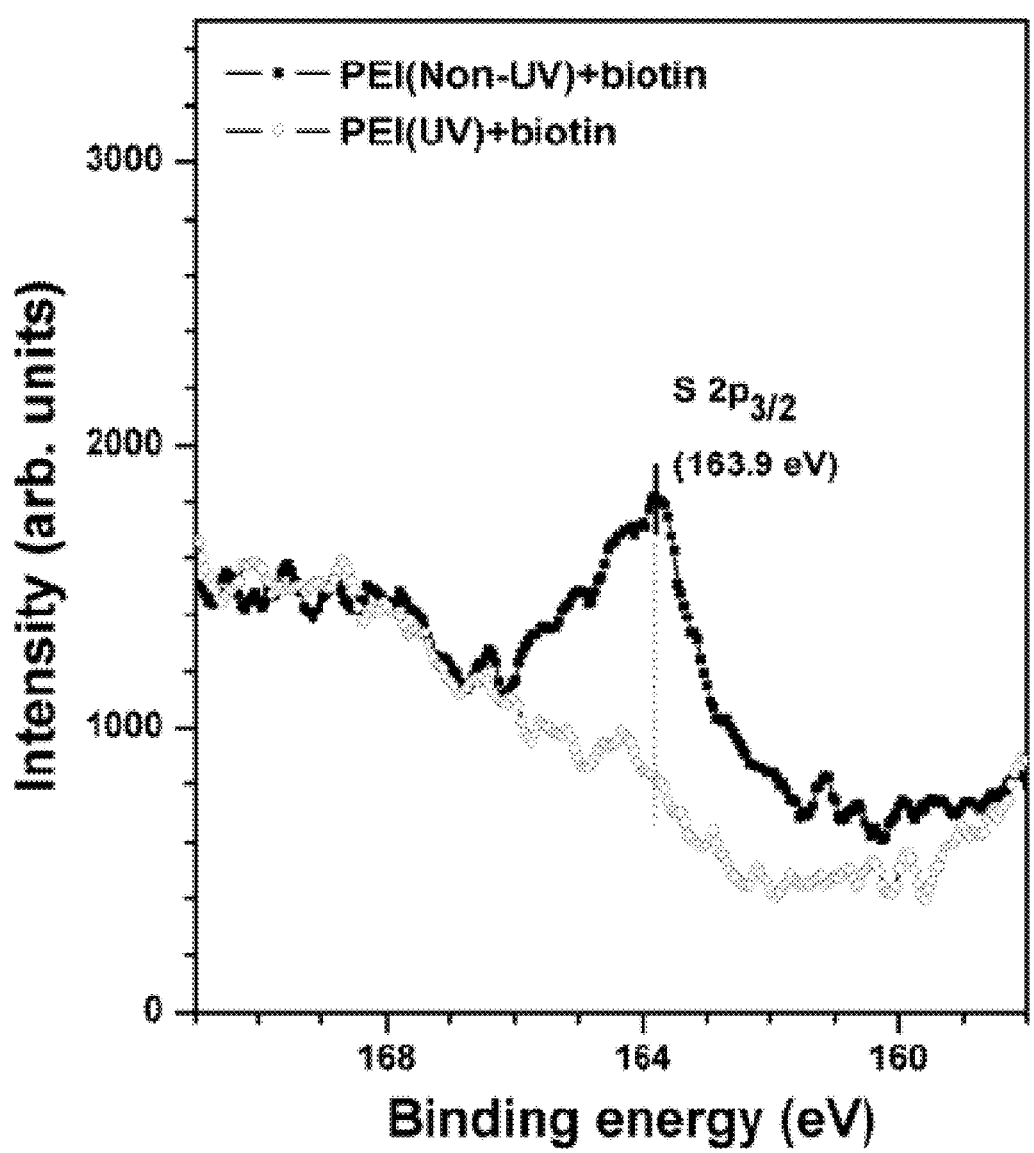
FIG. 4 illustrates an AR-XPS spectrum illustrating an effect of UV with respect to immobilization of biotin on a PEI layer.

A S2p spectrum having splitting of 1.2 eV, which was acquired from the UV irradiatied part and the blocked area is shown in FIG. 4. The AR-XPS result represents that there was a significant difference between the UV irradiated part and a UV blocked area. A S2p peak at 164.0 eV originated from $S^{2+}$ form sulfur binding with the biotin molecule. This represents that biotin was bound with the UV blocking area.

According to the results of the fluorescent microscopy and the AR-XPS, the surface of the PEI layer on the silicon oxide film was successively modified by short wavelength UV irradiation (254 nm). Conjugation of AMCA-X,SE and NHS-Sulfo-biotin was not verified through the fluorescent microscopy and AR-XPS, while the effect of UV irradiation was verified through conjugation of AMCA-X,SE and NHS-Sulfo-biotin and amine of the PEI layer.

According to the result, modification of the PEI surface may be used to control immobilization of the chemical linker such as NHS-Sulfo-biotin. Therefore, it is possible to control attachment of a specific chemical linker by modifying a specific part of an entire polymer layer.

Experimental Example 2

Analysis of Biotin-Streptabidin Binding on Pattern

In order to immobilize streptabidin protein on the biosensor substrate pattern fabricated in Embodiment 1, the specimen prepared in Embodiment 1 was dipped in the solution in which 2.2 mg NHS-Sulfo-Biotin was dissolved in 500 µl PBS buffer (pH 7.4) for 30 minutes.

After 100 µl Dynabeads-280 (Invitrogen Dynal AS, Oslo, Norway) suspension which is a magnetic particle coated with streptabidin on the surface thereof was cleansed with the PBS buffer, the cleansed magnetic particle of 100 µl was again floated with the 100 µl PBS buffer, such that a magnetic particle solution of 100 µl was prepared. At room temperature, after a specimen bound with the biotin was dipped in the magnetic particle solution for 30 minutes, the specimen was drawn out and cleansed with tertiary distilled water and was observed by using the fluorescent microscopy. A fluorescence reaction was observed by using the above-mentioned AMCA-X,SE.

Figure 5:
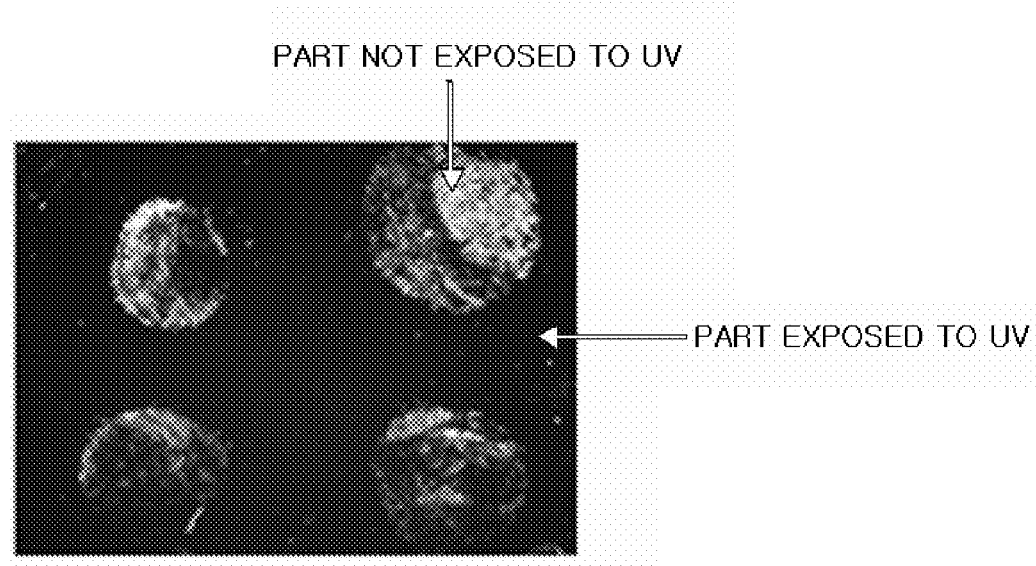
FIG. 5 is a photograph illustrating immobilization of a magnetic particle coated with streptabidin on a pattern on a biosensor substrate according to a preferred embodiment of the present invention.

As shown in FIG. 5, a fluorescence signal of a streptabidin magnetic particle selectively bound to biotin immobilized on the pattern on the surface can be verified.

What is claimed is:

1. A method for fabricating a pattern on a biosensor substrate, comprising:
   depositing a silicon oxide film on a substrate;
   forming a polyethylenimine layer on the silicon oxide film;
   selectively masking a site where a biosubstance is to be immobilized onto the polyethylenimine layer; and
   irradiating the substrate by using ultraviolet rays.

2. The method for fabricating a pattern on a biosensor substrate according to claim 1, wherein the substrate is comprised of any one selected from the group consisting of silicon, quartz, and glass.

3. The method for fabricating a pattern on a biosensor substrate according to claim 1, wherein the masking is performed by using any one selected from the group consisting of a teflon tape, an aluminum foil, and an enamelled copper wire.

4. The method for fabricating a pattern on a biosensor substrate according to claim 1, wherein the irradiation is performed for 10 minutes to 1 hour by using ultraviolet rays of 220 nm to 300 nm.

* * * * *